United States Patent
Ho et al.

(10) Patent No.: US 10,527,504 B2
(45) Date of Patent: Jan. 7, 2020

(54) TRANSPARENT PRESSURE SENSOR AND MANUFACTURING METHOD THEREOF

(71) Applicant: Winbond Electronics Corp., Taichung (TW)

(72) Inventors: Yu-Hsuan Ho, Taichung (TW); Ming-Chih Tsai, Taichung (TW); Ming-Hung Hsieh, Taichung (TW)

(73) Assignee: Winbond Electronics Corp., Taichung (TW)

( * ) Notice: Subject to any disclaimer, the term of this patent is extended or adjusted under 35 U.S.C. 154(b) by 0 days.

(21) Appl. No.: 15/679,161

(22) Filed: Aug. 17, 2017

(65) Prior Publication Data

US 2018/0209859 A1    Jul. 26, 2018

(30) Foreign Application Priority Data

Jan. 25, 2017  (TW) ............... 106102887 A

(51) Int. Cl.
| | |
|---|---|
| G01L 1/14 | (2006.01) |
| B32B 7/02 | (2019.01) |
| B32B 15/02 | (2006.01) |
| G01N 27/30 | (2006.01) |
| B82Y 30/00 | (2011.01) |
| B82Y 15/00 | (2011.01) |

(52) U.S. Cl.
CPC .............. *G01L 1/148* (2013.01); *G01L 1/146* (2013.01); *B32B 7/02* (2013.01); *B32B 15/02* (2013.01); *B32B 2307/20* (2013.01); *B32B 2307/412* (2013.01); *B82Y 15/00* (2013.01); *B82Y 30/00* (2013.01); *G01N 27/305* (2013.01)

(58) Field of Classification Search
USPC .......................................... 73/780
See application file for complete search history.

(56) References Cited

U.S. PATENT DOCUMENTS

| | | | |
|---|---|---|---|
| 5,305,017 | A | 4/1994 | Gerpheide |
| 5,565,658 | A | 10/1996 | Gerpheide et al. |
| 5,861,875 | A | 1/1999 | Gerpheide |
| 8,266,971 | B1 | 9/2012 | Jones |
| 8,598,893 | B2 | 12/2013 | Camus |

FOREIGN PATENT DOCUMENTS

| | | |
|---|---|---|
| CN | 101582303 | 11/2009 |
| CN | 102187413 | 9/2011 |
| CN | 103947002 | 7/2014 |
| CN | 104040639 | 9/2014 |

(Continued)

OTHER PUBLICATIONS

Translation of JP 2003-075277A.*

(Continued)

*Primary Examiner* — Nathaniel T Woodward
(74) *Attorney, Agent, or Firm* — JCIPRNET

(57) ABSTRACT

A transparent pressure sensor and a manufacturing method thereof are provided. The transparent pressure sensor includes several layers of transparent electrodes, at least one pressure-sensitive deformation layer between the transparent electrodes, and a metal oxide layer. Each layer of the transparent electrodes is composed of nanowires, and the metal oxide layer is disposed in a space among the nanowires.

6 Claims, 6 Drawing Sheets

(56) References Cited

FOREIGN PATENT DOCUMENTS

| | | | |
|---|---|---|---|
| CN | 104407749 | | 3/2015 |
| CN | 104575660 | | 4/2015 |
| CN | 104781642 | | 7/2015 |
| CN | 205158318 | | 4/2016 |
| JP | H111505641 | | 5/1999 |
| JP | 2003-075277 A | * | 3/2003 |
| JP | 2003075277 | | 3/2003 |
| JP | 2013182871 | | 9/2013 |
| JP | 2015045623 | | 3/2015 |
| JP | 2015135933 | | 7/2015 |
| JP | 2015200600 | | 11/2015 |
| JP | 2016118545 | | 6/2016 |
| TW | 201539279 | | 10/2015 |
| WO | 2007020781 | | 2/2007 |
| WO | WO 2007/020781 | * | 2/2007 |
| WO | 2010018734 | | 2/2010 |
| WO | WO 2010/018734 | * | 2/2010 |

OTHER PUBLICATIONS

Translation of WO 2010/018734.*
Translation of WO 2007/020781.*
Chen et al., "Thermally Stable Silver Nanowire-Polyimide Transparent Electrode Based on Atomic Layer Deposition of Zinc Oxide on Silver Nanowires", Adv. Funct. Mater. 2015, 25, 7512-7520 (Year: 2015).*
Jun et al., "High-Performance Low-Temperature Solution-Processable ZnO Thin Film Transistors by Microwave-Assisted Annealing ", J. Mater. Chem., 2011, 21, 1102-1108 (Year: 2011).*
Office Action of Japan Counterpart Application, dated Jun. 26, 2018, pp. 1-6.
Ye et al., "Metal Nanowire Networks: The Next Generation of Transparent Conductors", Advanced Materials, Sep. 23, 2014, pp. 1-9.
"Office Action of China Counterpart Application," dated Sep. 24, 2019, p. 1-p.9.

* cited by examiner

TRANSPARENT PRESSURE SENSOR AND MANUFACTURING METHOD THEREOF

CROSS-REFERENCE TO RELATED APPLICATION

This application claims the priority benefit of Taiwan application serial no. 106102887, filed on Jan. 25, 2017. The entirety of the above-mentioned patent application is hereby incorporated by reference herein and made a part of this specification.

BACKGROUND OF THE INVENTION

Field of the Invention

The invention relates to a pressure sensing technique and more particularly relates to a pressure sensor and a manufacturing method thereof.

Description of Related Art

In recent, the pressure-sensitive layer in the pressure sensor is mostly formed by mixing conductive particles in a resin. When pressure is applied, the thickness of the pressed part decreases, which reduces the distance between the conductive particles and causes the output resistance to drop. In other words, the conductivity of the pressed part is raised so as to achieve the function of the pressure-sensitive deformation layer. Such pressure sensors require higher conductivity. Therefore, the electrodes are mostly metal layers. Consequently, an overall transparent pressure sensor is not possible.

SUMMARY OF THE INVENTION

The invention provides a transparent pressure sensor, which senses a pressure by a change in capacitance and has a structure that is overall transparent.

The invention further provides a manufacturing method of a transparent pressure sensor for manufacturing a pressure sensor that is overall transparent.

A transparent pressure sensor of the invention includes a plurality of layers of transparent electrodes, at least one pressure-sensitive deformation layer, and a metal oxide layer. The transparent electrode includes a plurality of nanowires. The pressure-sensitive deformation layer is located between two layers of the transparent electrodes. The metal oxide layer is disposed in a space among the nanowires of each layer of the transparent electrodes.

Another transparent pressure sensor of the invention includes a first transparent electrode including a plurality of nanowires, a second transparent electrode including a plurality of nanowires, a pressure-sensitive deformation layer located between the first and the second transparent electrodes, and a metal oxide layer disposed in a space among the nanowires. The first transparent electrode has a first end and the second transparent electrode has a second end.

A manufacturing method of a transparent pressure sensor of the invention includes: performing a first printing process to form a plurality of transparent electrodes including a plurality of nanowires wherein the semiconductor colloid layer includes a solvent and a metal oxide precursor; performing a second printing process to form a semiconductor colloid layer in a space among the nanowires; performing a third printing process to form a pressure-sensitive deformation layer on the semiconductor colloid layer and the transparent electrode; repeating the first to the third printing processes; and then performing a thermal process to remove the solvent in the semiconductor colloid layer and reduce the metal oxide precursor to a metal oxide.

Based on the above, according to the invention, the transparent electrodes composed of nanowires and the transparent pressure-sensitive deformation layer are utilized, and thus the pressure sensor that is overall transparent can be manufactured. Moreover, the space among the nanowires is filled with the semiconductor colloid layer during the manufacturing processes. Therefore, the bonding between adjacent nanowires is enhanced to improve the stability and conductivity of the wires and prevent the problem of broken wires in the subsequent printing processes of the pressure-sensitive deformation layer.

To make the aforementioned and other features and advantages of the invention more comprehensible, several embodiments accompanied with figures are described in detail as follows.

BRIEF DESCRIPTION OF THE DRAWINGS

The accompanying drawings are included to provide a further understanding of the invention, and are incorporated in and constitute a part of this specification. The drawings illustrate exemplary embodiments of the invention and, together with the description, serve to explain the principles of the invention.

DESCRIPTION OF THE EMBODIMENTS

Figure 1:
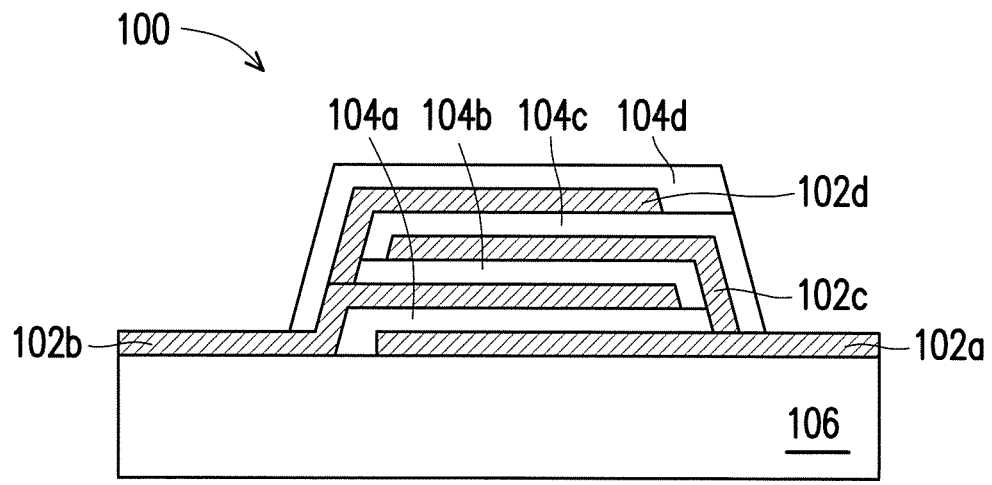
FIG. 1 is a cross-sectional view of a transparent pressure sensor according to an embodiment of the invention.

Referring to FIG. 1, in this embodiment, a transparent pressure sensor 100 includes a plurality of layers of transparent electrodes 102a, 102b, 102c, and 102d, a plurality of pressure-sensitive deformation layers 104a, 104b, 104c, and 104d, and a metal oxide layer. All the components shown in FIG. 1 are formed on a substrate 106. The pressure-sensitive deformation layer 104a is located between the transparent electrodes 102a and 102b, the pressure-sensitive deformation layer 104b is located between the transparent electrodes 102b and 102c, the pressure-sensitive deformation layer 104c is located between the transparent electrodes 102c and 102d, and the pressure-sensitive deformation layer 104d covers the transparent electrode 102d. When a pressure is applied, the transparent pressure sensor 100 of this embodiment senses the pressure based on a change in capacitance, which results from a change of a distance between the transparent electrodes 102a, 102b, 102c, and 102d caused by the pressure. For example, when the pressure is applied, the pressure-sensitive deformation layers 104a, 104b, and 104c at the pressed part become thinner, which causes the capacitance therebetween to decrease. Because the transparent electrodes 102a and 102c are electrically connected to one end while the transparent electrodes 102b and 102d are electrically connected to another end, a capacitance of the transparent pressure sensor 100 may be measured by connecting an electric meter to the aforementioned two ends to obtain the capacitances of the pressure-sensitive deformation layers 104a, 104b, and 104c.

Unlike a resistive pressure sensor that needs to take conductivity into account, the pressure sensor of this embodiment achieves overall transparency simply with use of the transparent electrodes 102a, 102b, 102c, and 102d. Moreover, the transparent pressure sensor of this embodiment only requires the pressure-sensitive deformation layers 104a, 104b, and 104c between the transparent electrodes 102a, 102b, 102c, and 102d. The pressure-sensitive deformation layer 104d that covers the transparent electrode 102d may serve as a protective or buffering structure, or be omitted.

Figure 2:
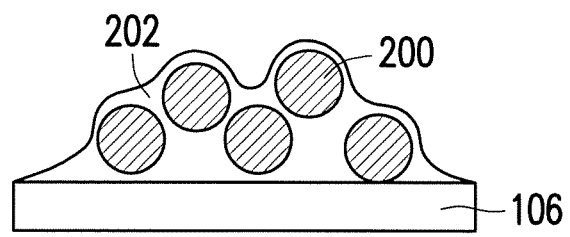
FIG. 2 is an enlarged cross-sectional view of a transparent electrode of the transparent pressure sensor of FIG. 1.

In this embodiment, a cross-sectional view of any of the transparent electrodes 102a, 102b, 102c, and 102d is shown in FIG. 2. One layer of the transparent electrode is composed of a plurality of nanowires 200, and a metal oxide layer 202 is disposed in a space among the nanowires 200. A material of the nanowires 200 is a metal such as gold, silver, copper, and so on; and a material of the metal oxide layer 202 is titanium dioxide, zinc oxide, or tungsten oxide, for example. In FIG. 2, the metal oxide layer 202 fills the space among the nanowires 200. In one embodiment, the metal oxide layer 202 may be formed by using a colloid layer containing a metal oxide precursor to accumulate in the space and at junctions among the nanowires 200 through capillary phenomenon and then performing a heat treatment to reduce the metal oxide precursor. In addition, a thickness of the metal oxide layer 202 formed on a surface of the nanowire 200 is in a range of 0.1 nm to 10 nm, for example. Nevertheless, the invention is not limited thereto. Because the metal oxide layer 202 almost covers the nanowires 200, the metal oxide layer 202 may serve as a protective film of the nanowires 200. Moreover, the metal oxide layer 202 gathering at the junctions of the nanowires 200 also enhances the bonding among the nanowires 200 and thereby improves the stability and conductivity of the wires. The metal oxide layer 202 also increases the adhesion between the transparent electrodes and the substrate 106 and thereby improves the stability of the whole wire structure.

Figure 3:
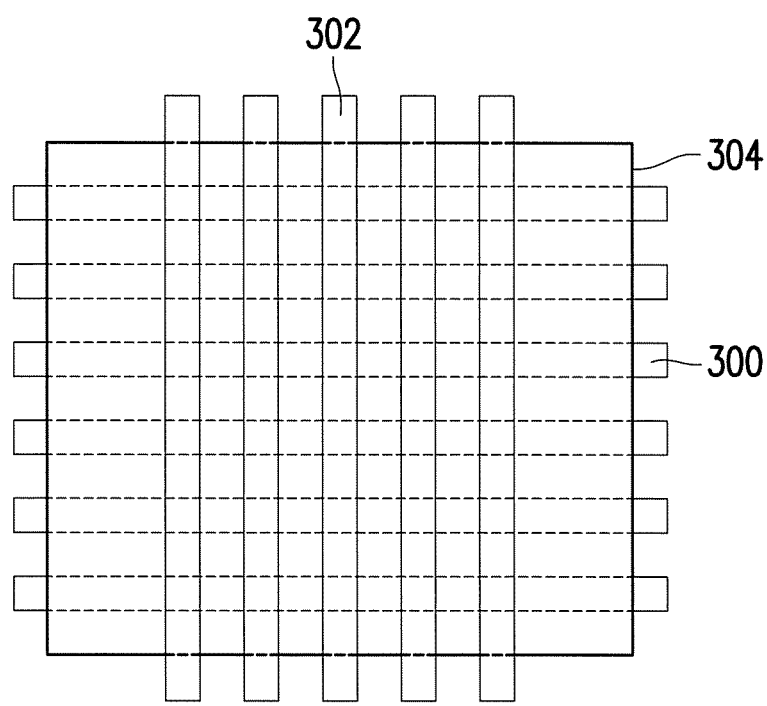
FIG. 3 is a plan view of a transparent pressure sensor according to another embodiment of the invention.

Please refer to FIG. 3. In order to facilitate understanding, some components are omitted from FIG. 3. Transparent electrodes 300 and 302 of the transparent pressure sensor are linear electrodes, and a pressure-sensitive deformation layer 304 is located between the two layers of transparent electrodes 300 and 302. The transparent electrodes 300 and 302 may be composed of a plurality of nanowires (200), and a metal oxide layer (202) is disposed in the space among the nanowires, as shown in FIG. 2. Thus, details thereof are not repeated hereinafter. In FIG. 3, the linear electrodes (i.e., 300 and 302) extend in different directions. Nevertheless, the invention is not limited thereto.

Figure 4A:
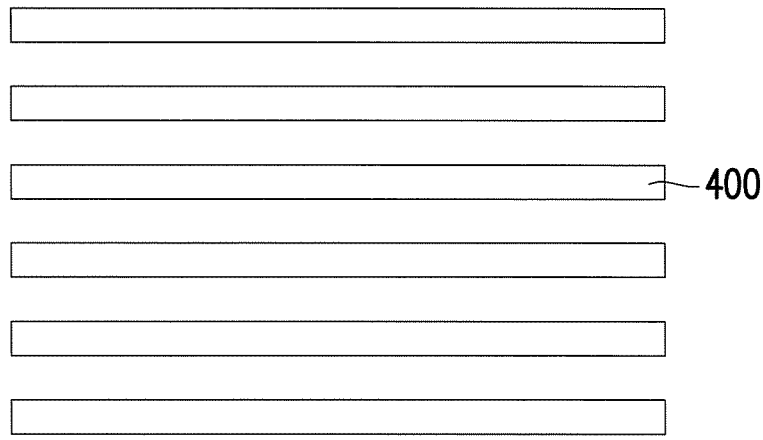
FIG. 4A to FIG. 4E are plan views showing a process flow of manufacturing a transparent pressure sensor according to yet another embodiment of the invention.

Regarding the plan views that illustrate a manufacturing method of the invention, first, referring to FIG. 4A, a first printing process is performed to form a layer of a transparent electrode 400 composed of a plurality of nanowires, wherein a material of the nanowires is gold, silver, or copper, for example. The first printing process may be 3D printing.

Figure 4B:
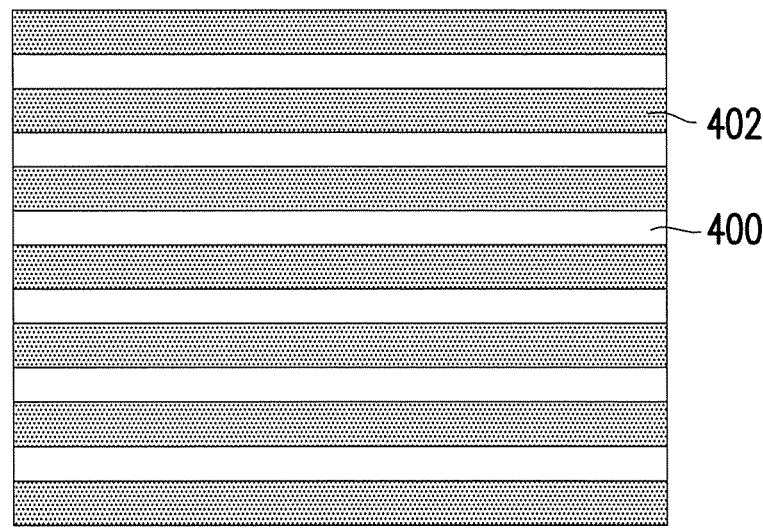

Then, referring to FIG. 4B, a second printing process is performed to form a semiconductor colloid layer 402 in a space among the transparent electrode 400, wherein the semiconductor colloid layer 402 includes a solvent and a metal oxide precursor. The metal oxide precursor is a titanium dioxide precursor, a zinc oxide precursor, or a tungsten oxide precursor; and the solvent is water, for example. In this embodiment, because of a capillary phenomenon, the semiconductor colloid layer 402 accumulates in the space among the transparent electrode 400. The second printing process may be 3D printing. After the second printing process is finished, the semiconductor colloid layer 402 is almost dry.

Figure 4C:
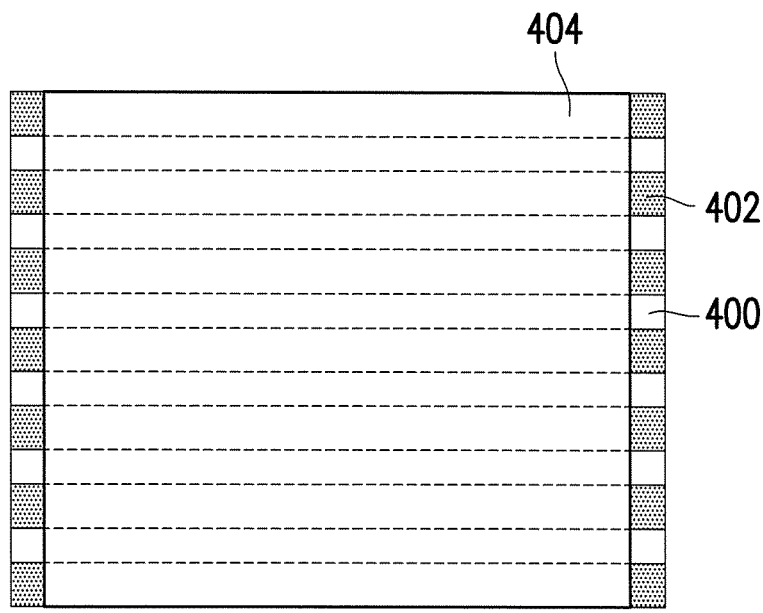

Next, referring to FIG. 4C, a third printing process is performed to form a pressure-sensitive deformation layer 404 on the semiconductor colloid layer 402 and the transparent electrode 400. The third printing process may be 3D printing. In general, the semiconductor colloid layer 402 and the pressure-sensitive deformation layer 404 contain insoluble materials and solvents. Therefore, even if the third printing process is performed immediately after the second printing process, the semiconductor colloid layer 402 and the pressure-sensitive deformation layer 404 do not interfere with each other.

Figure 4D:
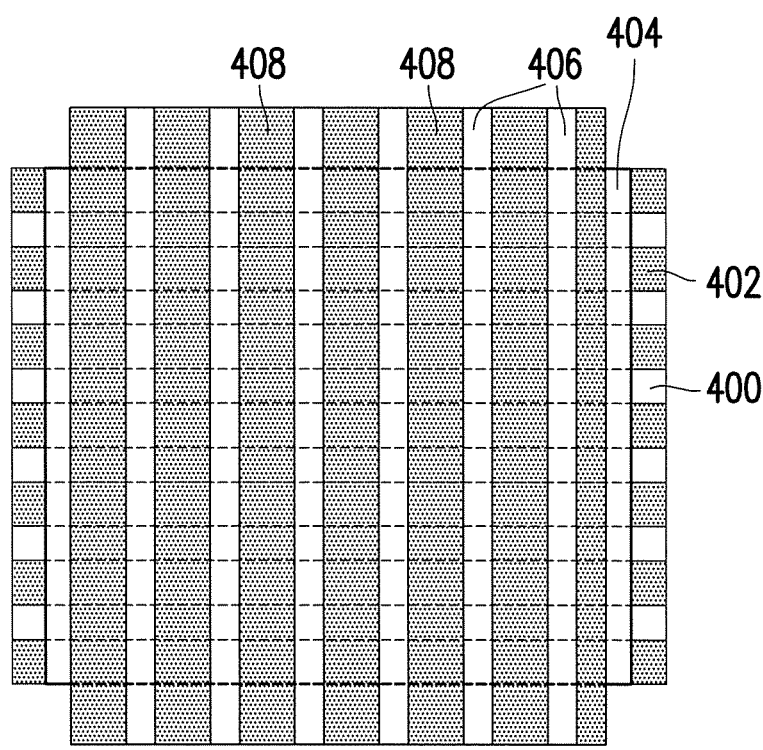

The structure as shown in FIG. 4D is obtained by repeating the first and the second printing processes described above, in which a transparent electrode 406 and a semiconductor colloid layer 408 are shown. As can be seen from FIG. 4D, the transparent electrodes 400 and 406 respectively in the upper and lower layers are arranged in an array. Thus, this embodiment is also applicable to a pressure-sensitive touch device, such as a touch panel.

Figure 4E:
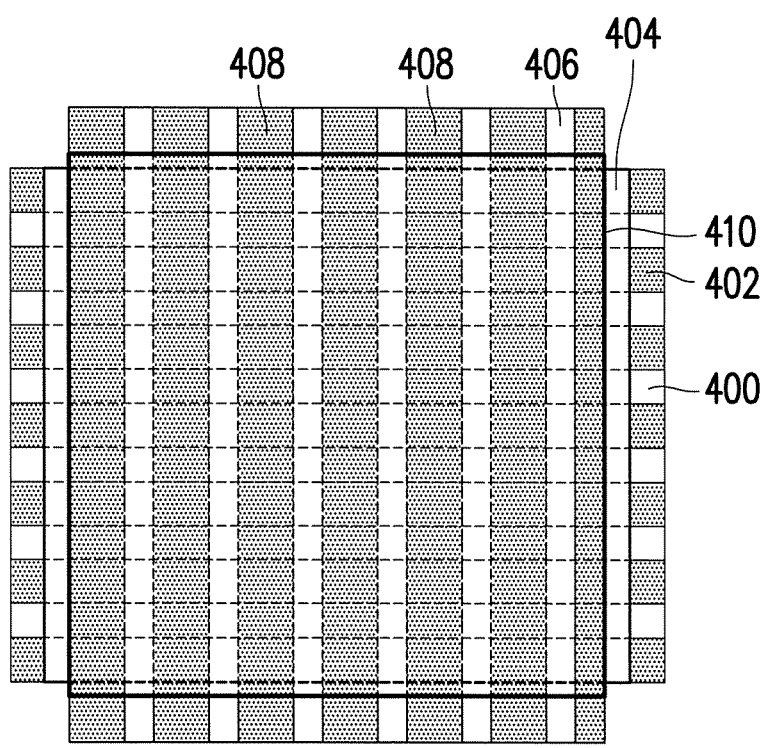

Thereafter, the third printing process is performed again to obtain the structure as shown in FIG. 4E, which shows another pressure-sensitive deformation layer 410. In this embodiment, the layers are formed by printing. Therefore, the first to the third printing processes may be repeated as required to manufacture a transparent pressure sensor that has multiple layers. Then, a thermal process is performed to remove the solvents in the semiconductor colloid layers 402 and 408 and to reduce the metal oxide precursor to a metal oxide, such as titanium dioxide, zinc oxide, or tungsten oxide. A heat treatment temperature of the thermal process is in a range of 50° C. to 200° C., for example. In addition, a low temperature baking process at 50° C. to 200° C. may be selectively performed after the second printing process, and the structure is left for 10 minutes to 20 minutes, so as to stabilize and cure the semiconductor colloid layer 402 and/or 408. Because the temperatures of all the thermal processes performed in this embodiment fall in a low temperature heating range, this embodiment is applicable to a flexible board of plastic.

An actual example of manufacturing the transparent pressure sensor is provided below for verifying the functions thereof.

Experimental Example

First, a metal ink containing nano-silver wires was sprayed and printed on two glass substrates respectively. Next, a semiconductor colloid containing a titanium dioxide precursor and water was sprayed and printed on the metal ink of one of the glass substrates, and then the two glass substrates were pressed together. Thereafter, the two glass substrates were baked at 150° C. for 1 hour to remove the solvent (water) and to reduce the titanium dioxide precursor to titanium dioxide. Thereby, a simple transparent pressure sensor having a light transmission rate of about 90% or more was completed, in which two layers of transparent electrodes composed of nano-silver wires with one semiconductor colloid layer therebetween were formed between the two glass substrates. During each of the printing (spraying) processes, the glass substrates were maintained at a temperature of about 80° C.

Pressure Sensing Test

Figure 5:
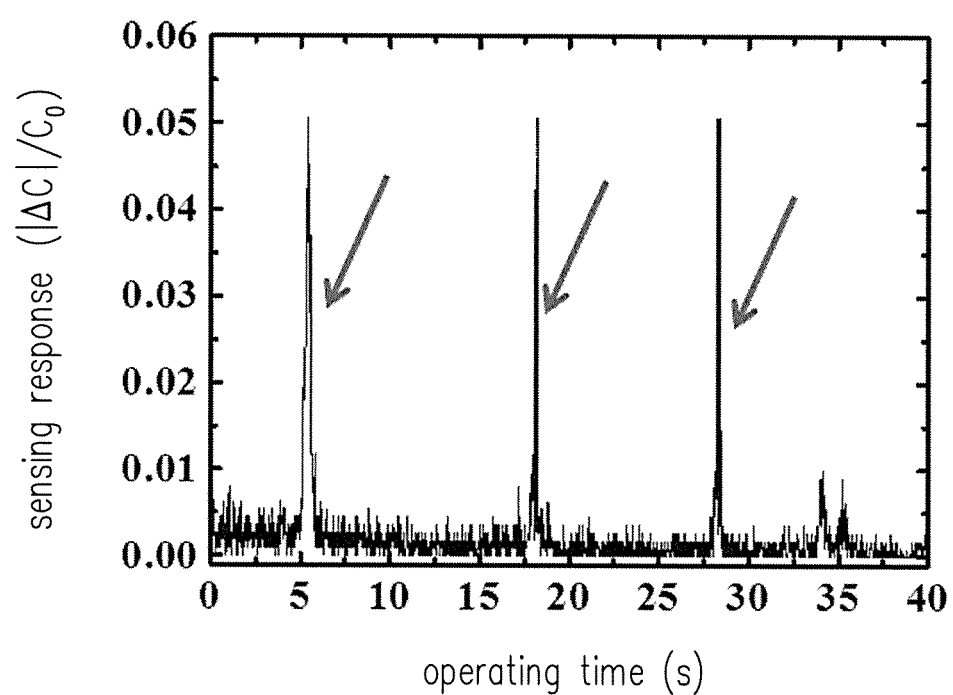
FIG. 5 is a pressure sensing graph according to an experimental example.

The capacitance of the transparent pressure sensor of the experimental example was measured, and the result showed that the capacitance was 0.2 nF when no pressure was applied, and the capacitance became 0.29 nF when the transparent pressure sensor was pressed. FIG. 5 is a graph showing a curve of an operating time with respect to sensing responses in the case of pressing the transparent pressure sensor of the experimental example three times, wherein the sensing response is $|\Delta C|/C_0$, $\Delta C$ is the difference in capacitance, and $C_0$ is the capacitance when no pressure is applied. The three arrows in FIG. 5 indicate that the transparent pressure sensor was pressed three times, which shows that the transparent pressure sensor is able to sense each pressing instantly.

Based on the above, in the invention, the transparent electrodes composed of nanowires and the pressure-sensitive deformation layer are utilized to manufacture the pressure sensor, and thus the pressure sensor that is overall transparent can be accomplished. Moreover, since the space among the nanowires is filled with the semiconductor colloid layer, the bonding between adjacent nanowires is enhanced to improve the stability and conductivity of the transparent electrodes and the problem of broken wires is prevented in the subsequent printing processes of the pressure-sensitive deformation layer.

It will be apparent to those skilled in the art that various modifications and variations can be made to the disclosed embodiments without departing from the scope or spirit of the invention. In view of the foregoing, it is intended that the invention covers modifications and variations of this disclosure provided that they fall within the scope of the following claims and their equivalents.

What is claimed is:

1. A transparent pressure sensor, comprising:
    a substrate;
    a plurality of layers of transparent electrodes disposed on the substrate, all of the plurality of layers of transparent electrodes are in direct contact with an end of the lowermost transparent electrode which is in direct contact with the substrate, and each of the plurality of layers of transparent electrodes comprises a plurality of nanowires;
    at least one pressure-sensitive deformation layer located between the layers of the transparent electrodes; and
    a metal oxide layer disposed in a space among the nanowires of each of the layers of the transparent electrodes,
    wherein the metal oxide layer is formed on a surface of each of the nanowires and has a thickness in a range of 0.1 nm to 10 nm.

2. The transparent pressure sensor according to claim 1, wherein each of the layers of the transparent electrodes is linear electrodes.

3. The transparent pressure sensor according to claim 2, wherein the linear electrodes in the layers of the transparent electrodes extend in different directions.

4. The transparent pressure sensor according to claim 2, wherein the linear electrodes in the layers of the transparent electrodes are arranged in an array.

5. A transparent pressure sensor, comprising:
    a substrate;
    a first transparent electrode having a first end disposed on the substrate, wherein the first transparent electrode comprises a plurality of layers of first linear electrodes, and all of the plurality of layers of first linear electrodes are electrically connected to the lowermost first linear electrode which is in direct contact with the substrate at the first end;
    a second transparent electrode having a second end disposed on the substrate, wherein the second transparent electrode comprises a plurality of layers of second linear electrodes, and all of the plurality of layers of second linear electrodes are electrically connected to the lowermost second linear electrode which is in direct contact with the substrate at the second end, wherein the first transparent electrode and the second transparent electrode comprise a plurality of nanowires;
    at least one pressure-sensitive deformation layer located between the first transparent electrode and the second transparent electrode; and
    a metal oxide layer disposed in a space among the nanowires,
    wherein the metal oxide layer is formed on a surface of each of the nanowires and has a thickness in a range of 0.1 nm to 10 nm.

6. The transparent pressure sensor according to claim 5, wherein the at least one pressure-sensitive deformation layer is further located between the first linear electrodes and between the second linear electrodes.

* * * * *